(12) United States Patent
Hara et al.

(10) Patent No.: US 8,526,075 B2
(45) Date of Patent: Sep. 3, 2013

(54) TRAY FOR IMAGE READING DEVICE

(75) Inventors: Masazumi Hara, Tokyo (JP); Hiroki Ishizuki, Tokyo (JP); Hiroaki Takeuchi, Tokyo (JP); Tatsuhiko Ochi, Tokyo (JP); Shuichi Hirano, Tokyo (JP); Jun Zheng, Tokyo (JP)

(73) Assignee: Satake Corporation, Tokyo (JP)

( * ) Notice: Subject to any disclaimer, the term of this patent is extended or adjusted under 35 U.S.C. 154(b) by 353 days.

(21) Appl. No.: 13/123,325

(22) PCT Filed: Oct. 1, 2009

(86) PCT No.: PCT/JP2009/005064
§ 371 (c)(1),
(2), (4) Date: Apr. 8, 2011

(87) PCT Pub. No.: WO2010/041388
PCT Pub. Date: Apr. 15, 2010

(65) Prior Publication Data
US 2011/0194159 A1 Aug. 11, 2011

(30) Foreign Application Priority Data
Oct. 9, 2008 (JP) .................................. 2008-262366

(51) Int. Cl.
*H04N 1/04* (2006.01)
(52) U.S. Cl.
USPC ........................... 358/474; 358/475; 358/449
(58) Field of Classification Search
USPC ......................... 358/474, 475, 449
See application file for complete search history.

(56) References Cited

U.S. PATENT DOCUMENTS

| 4,227,211 | A  | * | 10/1980 | Disbrow ...................... 348/164 |
| 7,035,464 | B2 | * | 4/2006  | Masuda ....................... 382/190 |
| 2003/0048927 | A1 | | 3/2003 | Sato et al. |
| 2009/0021751 | A1 | | 1/2009 | Jonasson Bjarang |

FOREIGN PATENT DOCUMENTS

| CN | 1407331 A1 | 4/2003 |
| EP | 1830176 A1 | 9/2007 |
| JP | 2002-162356 A | 6/2002 |
| JP | 2002-202265 A | 7/2002 |
| JP | 2002-365222 A | 12/2002 |
| JP | 2003-090799 A | 3/2003 |
| JP | 2003-090800 A | 3/2003 |
| JP | 2004-150956 A | 5/2004 |
| JP | 2004-156918 A | 6/2004 |

OTHER PUBLICATIONS

Notification of First Office Action issued by the Chinese Patent Office, mailed Oct. 18, 2012, in Chinese counterpart application No. 2009801370499.

* cited by examiner

*Primary Examiner* — Houshang Safaipour
(74) *Attorney, Agent, or Firm* — Law Office of Katsuhiro Arai

(57) ABSTRACT

A tray used to place granular materials on a reading surface of an image reading device has provided thereto a transparent bottom plate, a background vertically upstanding relative to the bottom plate, and reflective elements arranged at predetermined intervals parallel to the background. In order to enable an imaging means of the image reading device to receive a side view image of the granular materials in the thickness direction thereof with the granular materials placed on the bottom plate of the tray, the tray is provided with a technical means for bending and guiding, by the reflective elements, light from the granular materials in the thickness direction thereof to the direction of the optical axis of the imaging means.

8 Claims, 14 Drawing Sheets cross section A-A cross section A-A cross section A-A cross section A-A granular material cross section A-A cross section A-A

TRAY FOR IMAGE READING DEVICE

This application is the U.S. National Phase under 35 U.S.C. §371 of International Application PCT/JP2009/005064, filed Oct. 1, 2009, which claims priority to Japanese Patent Application No. 2008-262366, filed Oct. 9, 2008. The International Application was published under PCT Article 21(2) in a language other than English.

TECHNICAL FIELD

The present invention relates to an art for measuring shapes of granular materials such as grains, and more specifically, relates to a tray used for measuring dimensions of granular materials in three-axis directions, that is, length, width and thickness, using an image taken via an image reading device such as a scanner or a copying machine.

BACKGROUND ART

Conventionally, shapes of granular materials have been measured by taking images of granular materials using existing scanners and processing the taken image via personal computers and the like. Patent Document 1 and Patent Document 2 disclose alignment devices for placing multiple grains in an aligned state on a reading surface of a scanner, wherein the use of the alignment devices enable image of multiple grains to be taken easily and simultaneously.

However, in order to perform a highly accurate measurement in measuring the shapes of granular materials, it is necessary to measure not only the dimensions of the length (X) and the width (Y) but also the thickness (Z) of the materials, as shown in FIG. 12. However, the dimensions of the length and width of the materials could be measured by the conventional methods, but the dimension of the "thickness" could not be measured thereby.

Thus, development of methods for measuring not only the dimensions of the length and width of the granular materials but also the dimension of the "thickness" of the materials had been desired in order to measure the shapes of granular materials using images taken via scanners.

CITATION LIST

Patent Literature

[PTL 1] Japanese patent application laid-open publication No. 2004-150956
[PTL 2] Japanese patent application laid-open publication No. 2004-156918

SUMMARY OF INVENTION

Technical Problem

In light of the problems described above, the present invention aims at providing a tray for granular materials allowing the dimensions of granular materials in the three-axis directions, that is, the length, width and thickness, of the granular materials to be measured using an image taken via an image reading device such as a scanner.

Solution to Problem

In order to solve the problems mentioned above, the present invention provides a tray for placing granular materials on a reading surface of an image reading device such as a scanner, comprising: a transparent bottom plate, one or a plurality of backgrounds vertically upstanding relative to the bottom plate, and one or a plurality of reflective elements arranged at predetermined intervals in parallel with the background, wherein regarding granular materials placed between the background and the reflective element of the granular materials placed on the bottom plate of the tray, a light from a thickness direction of the granular materials is bent and guided via the reflective element to an optical axis direction of an imaging means of the image reading device, so that not only planar images in a longitudinal direction and a width direction of the granular materials but also a side view image in the thickness direction of the granular materials are received via the imaging means.

Further, in order to place granular materials efficiently on the bottom plate of the tray, the present invention provides an alignment plate fit from an upper direction to align the granular materials, comprising a protruded section for the background for covering the background, a protruded section for the reflective element disposed in parallel with the protruded section for the background for covering the reflective element, and a plurality of holes having a shape similar to the shape of the granular materials.

Furthermore, the present invention provides forming the reflective element of the tray using a prism or a mirror. Thus, the light from the side surface of the granular materials can be suitably entered to the imaging means via the reflective element.

In addition, the present invention provides placing the granular materials placed between the background and the reflective element at a predetermined distance from the reflective element via the alignment plate.

Furthermore, the present invention removes the bottom plate from the tray, so that granular materials are placed directly on the reading surface of the image reading device for measurement.

Advantageous Effects of Invention

The present invention enables to measure not only the dimensions of length and width of granular materials obtained via planar surface portions of the materials but also the dimension of the thickness obtained via a side surface portion thereof in order to measure the shapes of granular materials using images taken in via image reading devices. Therefore, the present invention enables to obtain accurate thickness information of granular materials and perform a highly accurate quality discrimination of granular materials.

According further to the present invention, the images of side surfaces of granular materials are taken by providing backgrounds and reference plates, so that not only the thickness dimension but also the color information and the like of the side surfaces of the granular materials can be obtained. Thus, the present invention enables to perform a highly accurate quality discrimination of granular materials based on color information of the planar surfaces and side surfaces of the materials.

Moreover, since the present invention enables the granular materials as measurement objects to be placed in an aligned manner using the alignment plate, the distance between the granular materials and the reflective elements can be maintained constant, and thereby, the influence that the distance may have on the measurement can be reduced.

DESCRIPTION OF EMBODIMENTS

Now, an embodiment for carrying out the present invention will be described with reference to the drawings.

Example 1

FIGS. 1 through 11 are explanatory views of example 1 according to the present invention.

Figure 1:
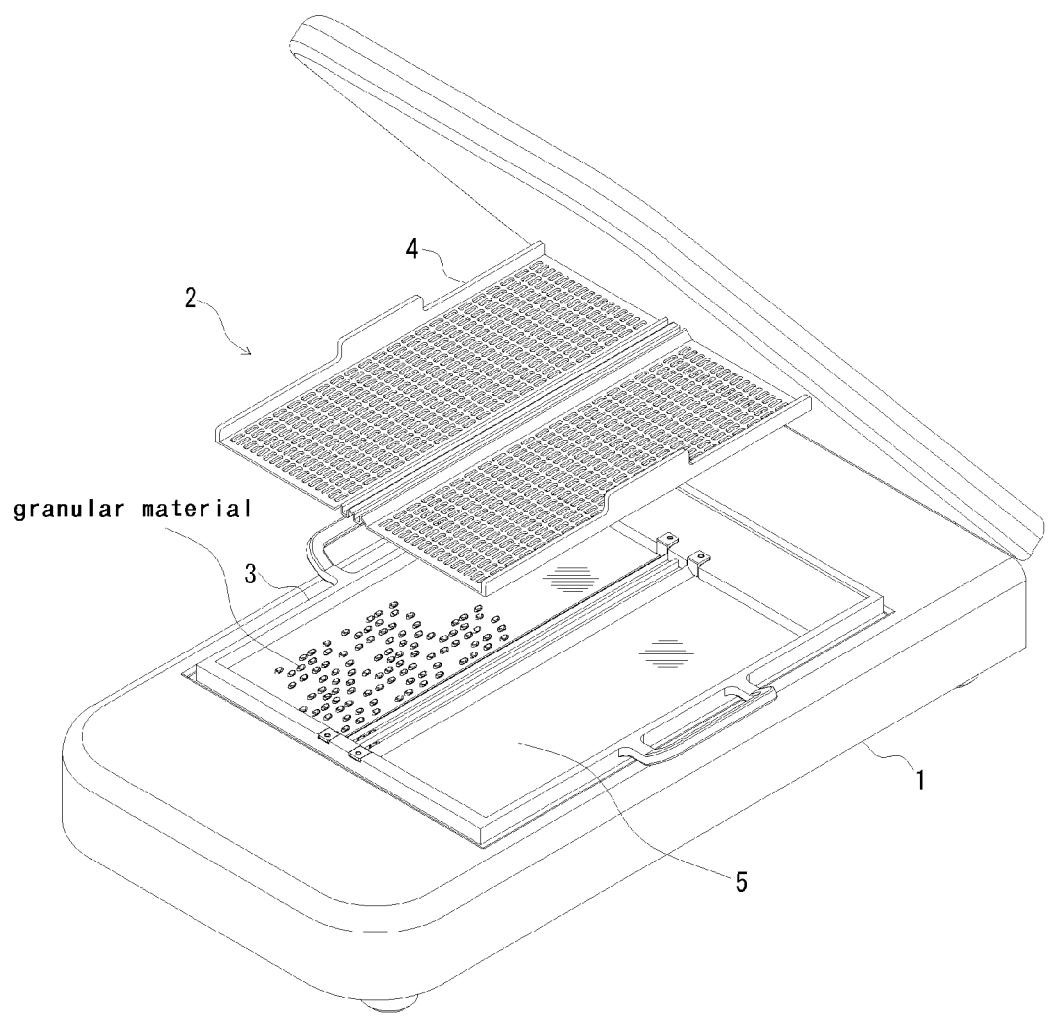
FIG. 1 is a perspective view showing a state in which a tray and an alignment plate are set to an image reading device according to example 1 of the present invention.

FIG. 1 is a perspective view showing the state in which an alignment device 2 composed of a tray 3 and an alignment plate 4 according to example 1 is set to an image reading device 1. An existing scanner can be used as the image reading device 1. A CANOSCAN 4400F manufactured by Canon Inc. was used in the present example.

Figure 2:
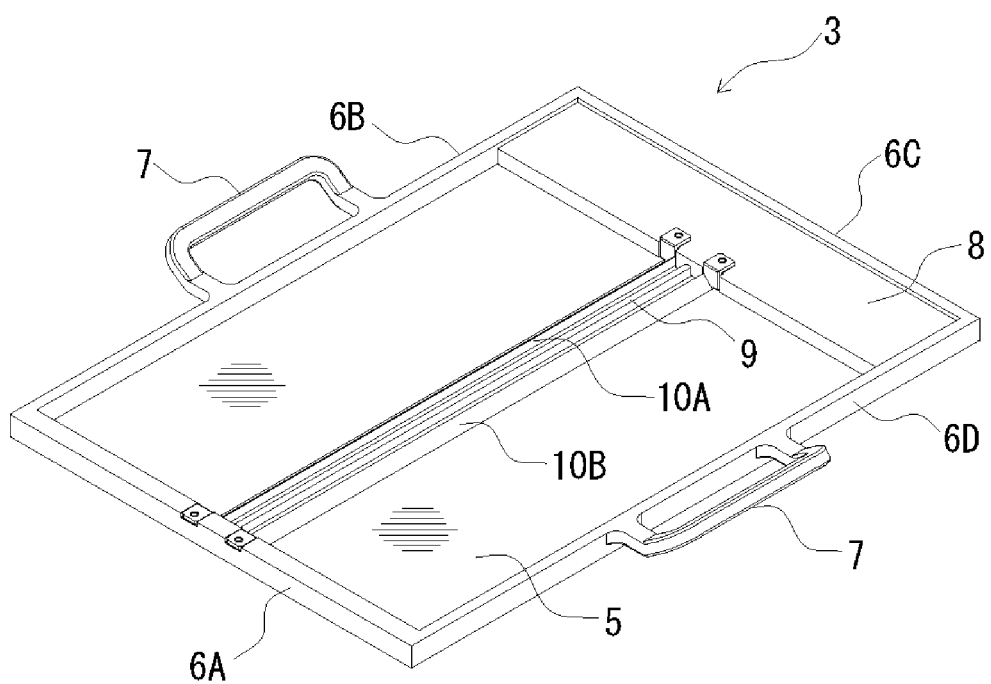
FIG. 2 is a perspective view of the tray according to example 1 of the present invention.
Figure 3:
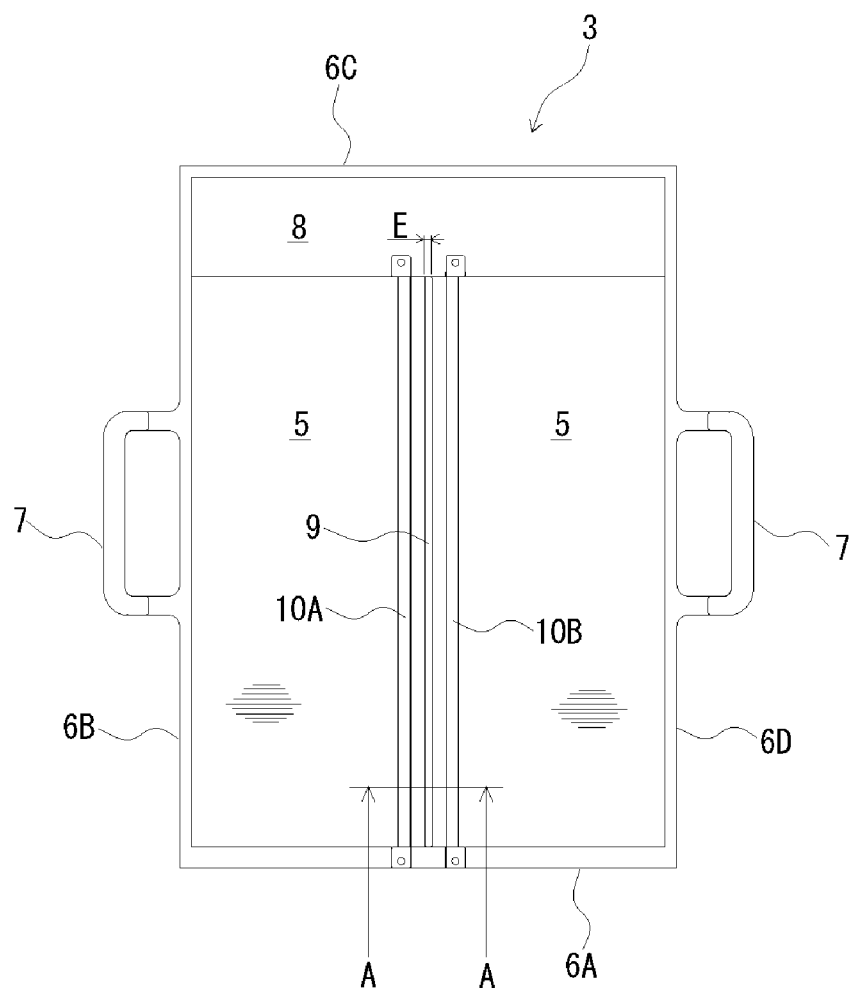
FIG. 3 is a plan view and a partial cross-sectional view of the tray according to example 1 of the present invention.
Figure 3:
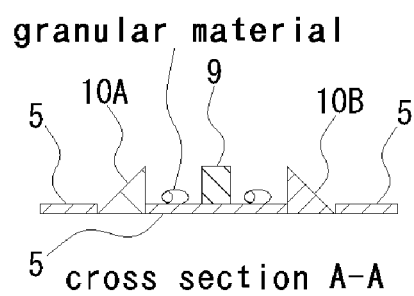
Figure 4:
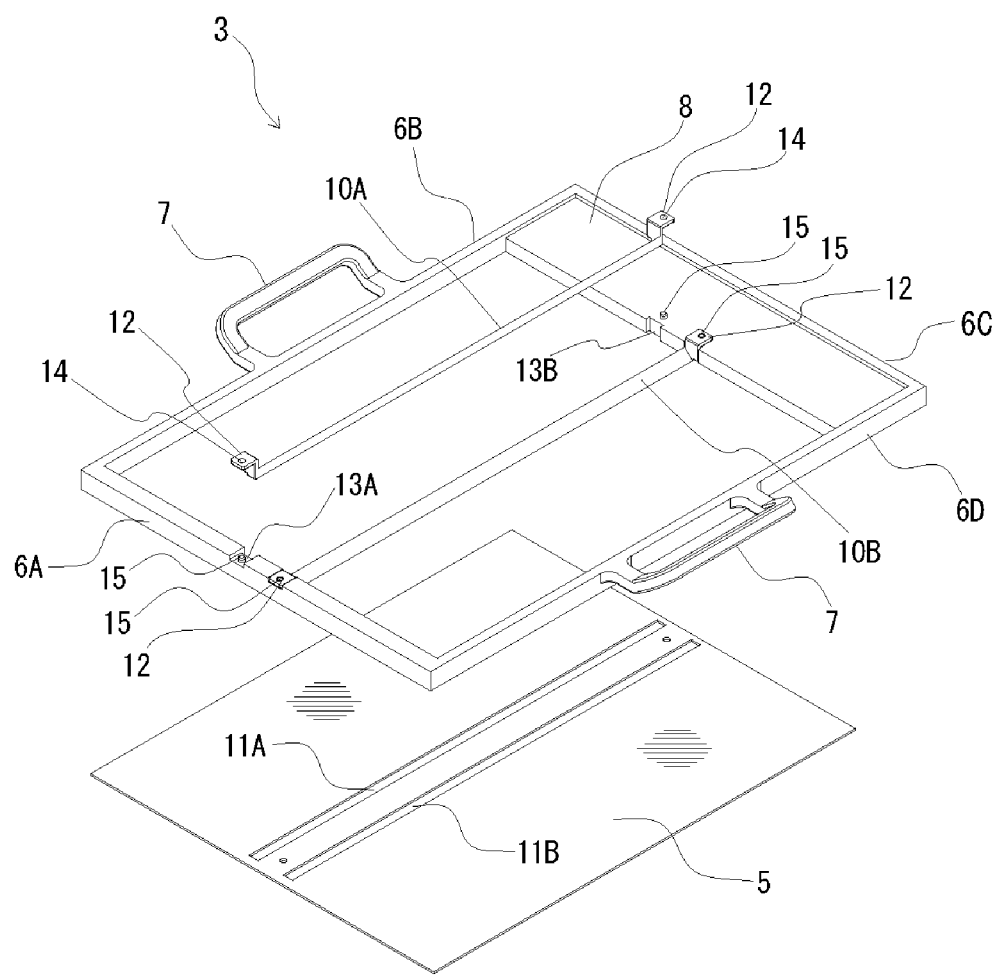
FIG. 4 is a view showing the structure of the tray according to example 1 of the present invention.

The tray 3 is formed to have a rectangular frame shape in planar view as shown in FIGS. 2, 3 and 4, which is composed of a bottom plate 5, side walls 6A, 6B, 6C and 6D, and handles 7.

The bottom plate 5 is a transparent plate which is formed for example of acrylic resin. As shown in FIG. 4, the bottom plate 5 is a single transparent plate having formed thereto slits 11A and 11B for inserting reflective elements 10A and 10B described in detail later. The bottom plate 5 is attached to a lower side of a rectangular frame formed of side walls 6A, 6B, 6C and 6D. Therefore, although not shown, grooves for receiving the bottom plate 5 are formed to the lower side of the side walls 6A, 6B, 6C and 6D. The bottom wall 5 can also be fixed directly to the lower end face of the side walls 6A, 6B, 6C and 6D.

The present example illustrated an example in which the bottom plate 5 is a single plate, but the bottom plate 5 can also be divided into three plates, separated into the section between the right side handle 7 and the reflective element 10B, the section between the left side handle 7 and the reflective element 10A, and the section between the reflective elements 10A and 10B, for example, or the bottom plate 5 can be divided into two plates, separated into the right side and the left side of a background 9 described in detail later. In other words, the bottom plate 5 is not necessarily formed of a single plate, and can be formed of a plurality of plates.

A reference plate 8 and a background 9 vertically upstanding relative to the bottom plate 5 are arranged on the space above the bottom plate 5 surrounded by the side walls 6A, 6B, 6C and 6D. For example, when the shape of granular materials or the like are measured by acquiring image signals of granular materials via the image reading device 1 and processing the image signals via a computer, the reference plate 8 is used for acquiring image information for correcting the image signals. But it can be omitted when only the three axes of the granular materials are to be measured. Further, the image information obtained by taking an image of the reference plate 8 is used for correcting the differences between multiple image reading devices.

Further, the position for arranging the reference plate 8 is not specifically restricted as long as it is on the space above the bottom plate 5, so the reference plate 8 can be arranged at any convenient area from the design point of view. Further, the shape of the reference plate 8 is not specifically restricted, but from the design point of view, it should preferably be rectangular. According to the present example, the reference plate 8 has a rectangular shape and is arranged so that one longitudinal end of the reference plate 8 is in contact with the side wall 6C.

The background 9 is disposed on the bottom plate 5 with the aim to facilitate recognition (extraction) of the granular materials via image processing such as binarization of the image when image of the granular materials is taken from the sides. The background 9 is arranged along a linear line connecting a center point of the side wall 6A and a center point of the side wall 6C according to the present example, wherein one end is in contact with the side wall 6A and the other end is in contact with the reference plate 8. If the reference plate 8 is not arranged, the other end should be extended to be in contact with the side wall 6C.

Further, the height of the background 9 does not have to be higher than the side walls 6A through 6D, and should be a few mm higher than the thickness (Z) of the granular materials being measured. Thus, the height of the background 9 may be varied according to the thickness of the granular materials being measured, wherein the height should be approximately 4 mm to 15 mm in general, and approximately 4 mm to 10 mm when the granular materials are rice grains. Further, the background 9 should be formed for example of resin.

The width of the background 9 ("E" of FIG. 3) should preferably be thin, though it depends on the material, since the space for placing granular materials to be measured will be reduced when the width thereof is too thick. However, the background 9 must have a width thick enough so that it is not transparent. However, according to the present example, the background 9 is formed of resin, and the width thereof is set to 3 mm. The color of the background 9 should be black, blue or other non-transparent colors, and should be different from the color of the granular materials to be measured. Therefore, when the granular materials are brown rice, the color of the background should be blue. The background 9 is arranged on the bottom plate 5 so that it is taken in the image as background of the granular materials to be measured in the image taken from the side of the granular materials. Further according to the present example, only the side surface of the granular materials and the background 9 are taken as image, so that the granular materials can be easily recognized (extracted) from the image.

According to the present example, a reflective element 10A is arranged parallel to the background 9. Unlike the background 9 which is disposed on the bottom plate 5, the reflective element 10A is attached by inserting to a slit 11A formed on the bottom plate 5, and arranged so that the bottom surface of the bottom plate 5 and the bottom surface of the reflective element 10A constitute a single plane as shown in the cross-sectional view of FIG. 3.

The method for mounting the reflective element 10A is not specifically restricted, but as shown in FIG. 4, it is possible to dispose mounting sections 12 on both ends of the reflective element 10A, one end of which can be fit to a groove 13A on the side wall 6A and the other end of which can be fit to a groove 13B of the reference plate 8. At this time, mounting can be facilitated by providing holes 14 on the mounting sections 12, the holes 14 being designed to fit to projections 15 disposed in correspondence to the groove 13A on the side wall 6A and the groove 13B on the reference plate 8. Further, if the reference plate 8 is not arranged, the other end of the reflective element 10A can be attached to the side wall 6C.

The reflective element 10B arranged opposite to the reflective element 10A with respect to the background 9 is attached in the same manner as the reflective element 10A.

Figure 5:
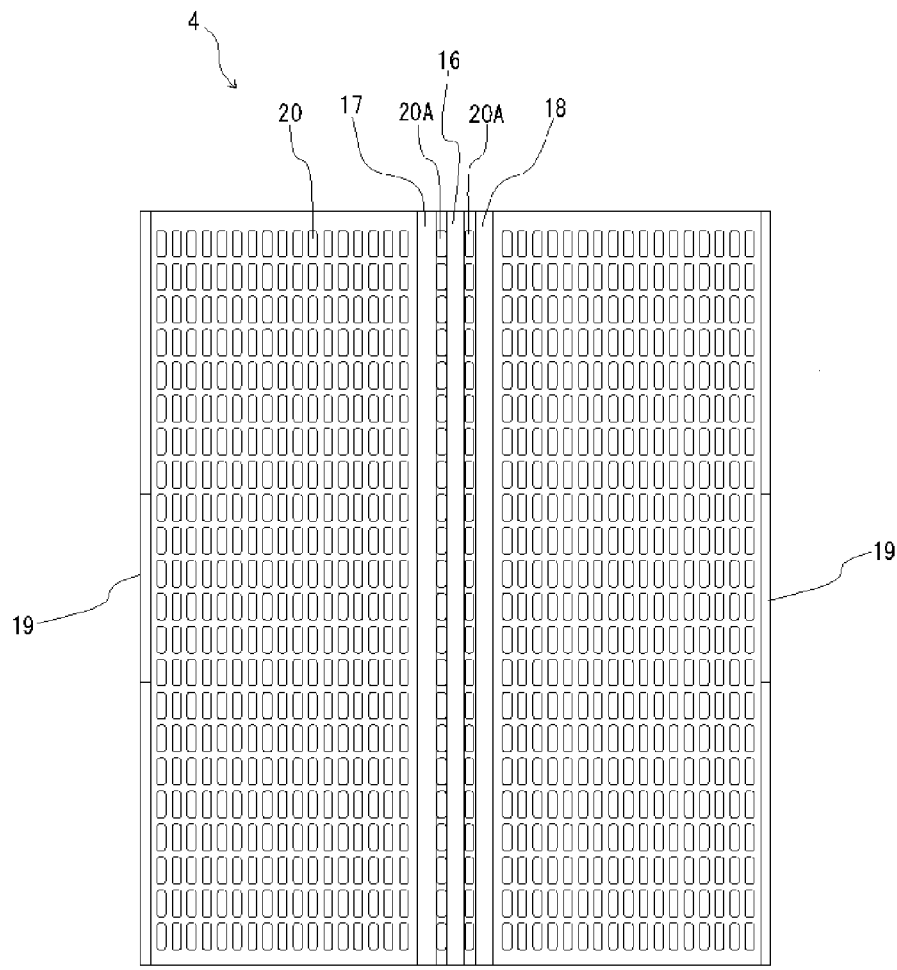
FIG. 5 is a plan view of an alignment plate according to example 1 of the present invention.
Figure 6:
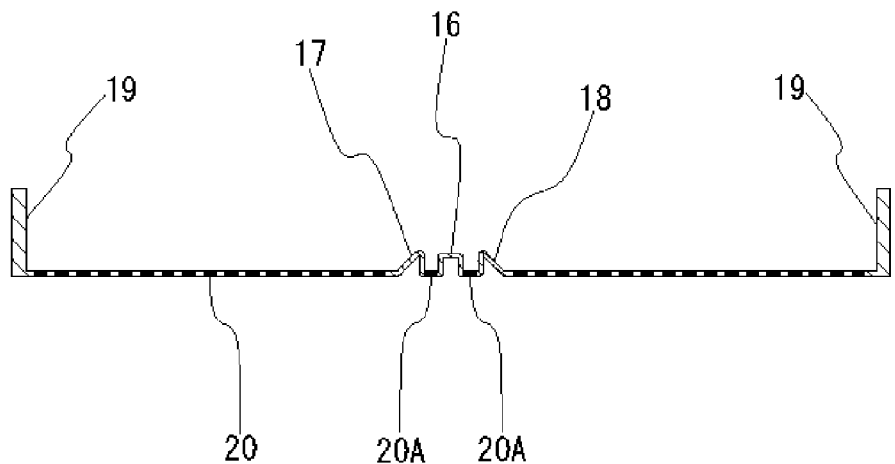
FIG. 6 is a cross-sectional view of the alignment plate according to example 1 of the present invention.

Next, an alignment plate 4 will be described. FIG. 5 is a plan view of the alignment plate 4, and FIG. 6 is a cross-sectional view thereof. The alignment plate 4 is a rectangular plate seen from the planar view, which is used by fitting from the upper side to a space surrounded by the side walls 6A, 6B and 6D of the tray 3 and one end of the reference plate 8.

A protruded section 16 for the background and protruded sections 17 and 18 for the reflective elements are provided on the alignment plate 4. The protruded section 16 for the background is a cover for covering the background 9 on the tray 3 when the alignment plate 4 is fit to the tray 3, and the protruded sections 17 and 18 for the reflective elements are for covering the reflective elements 10A and reflective elements 10B, respectively. Therefore, the cross-sectional shapes of the protruded section 16 for the background and protruded sections 17 and 18 for reflective elements are designed so that they are able to cover the background 9, the reflective element 10A and the reflective element 10B, respectively.

Further, handles 19 for facilitating handling of the alignment plate 4 are disposed in an upstanding state from the frame portion of the alignment plate 4. The handles 19 can be arbitrarily designed to user-friendly shapes.

A plurality of holes 20 are formed on the alignment plate 4. The holes 20 should preferably be formed in an orderly aligned manner as shown in the drawing rather than being formed randomly, considering the image processing performed in the subsequent process. Accordingly, when the image taken via the image reading device 1 is subjected to image processing in a personal computer or the like after the image is taken, the granular materials as objects of measurement can be extracted easily from the image. The shape of the holes 20 should preferably be similar to the shape of the granular materials being measured, and for example, when long-grain rice is subjected to measurement, the shape of each hole 20 should preferably be substantially rectangular with a length of 8.5 mm and a width of 2.8 mm, so as to enable the plurality of rice grains to be aligned with the long axes arranged in the same direction.

The depth of the holes 20 should vary according to the size of the granular materials being measured, but in order to prevent multiple granular materials from entering a single hole 20, the depth should preferably be somewhat shallower than the thickness of the granular materials. The holes 20 on the alignment plate 4 have no bottoms, and the holes are completely opened.

The functions and effects of the present example will now be described.

Figure 7:
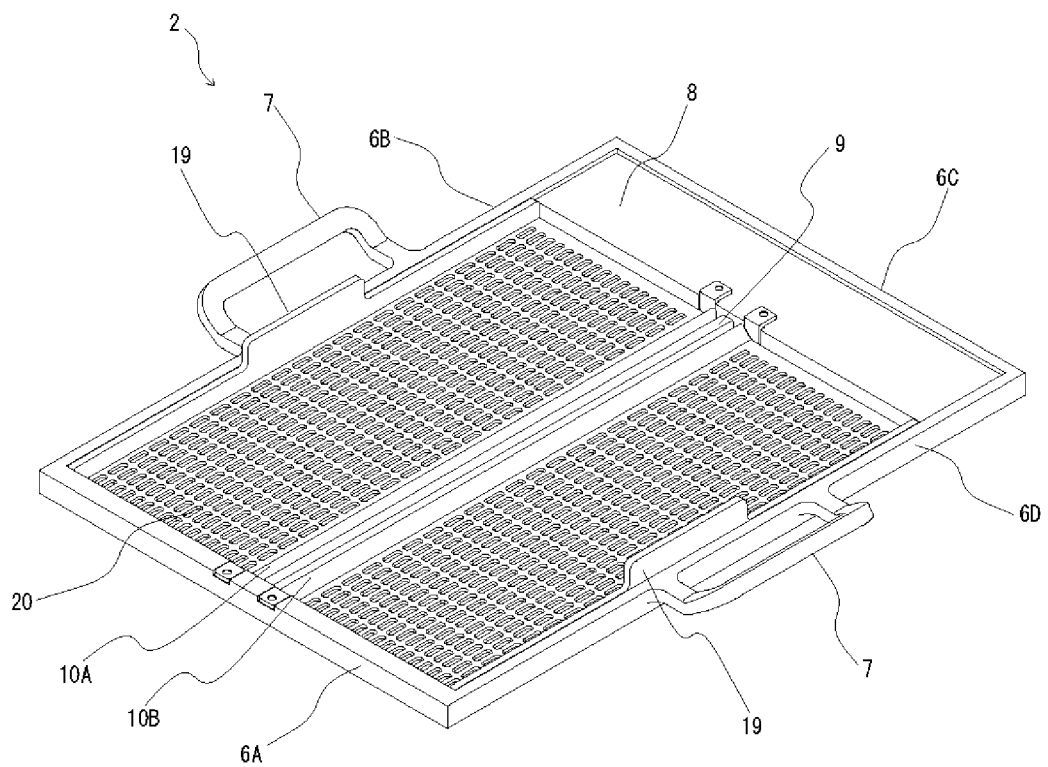
FIG. 7 is a perspective view showing the state in which the alignment plate is fit to the tray according to example 1 of the present invention.
Figure 8:
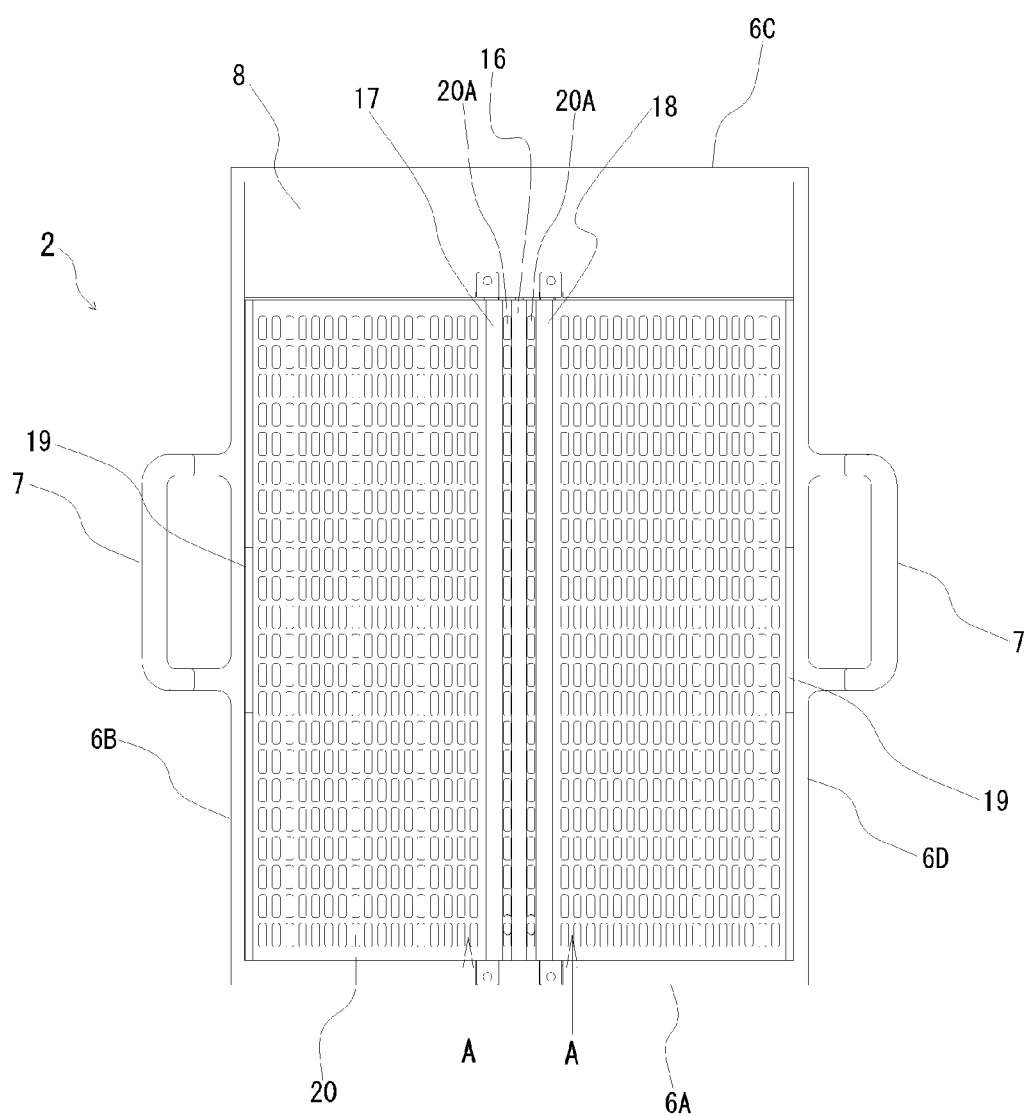
FIG. 8 is a plan view showing the state in which the alignment plate is fit to the tray according to example 1 of the present invention.

First, the alignment plate 4 is fit to the tray 3. By this operation, the alignment plate 4 is placed on top of the bottom plate 5 of the tray 3 (FIGS. 7 and 8). Next, a plurality of granular materials to be measured are poured into the alignment plate 4. At this time, granular materials are poured into areas between the protruded section 16 for the background and the protruded section 17 for the reflective element and between the protruded section 16 for the background and the protruded section 18 for the reflective element, so that the granular materials are also fit in the holes 20A arranged in those areas. Then, the tray 3 is shaken back and forth and around by holding the handles 7 of the tray 3 so that the granular materials are fit in the holes 20 and 20A on the alignment plate 4.

Figure 9:
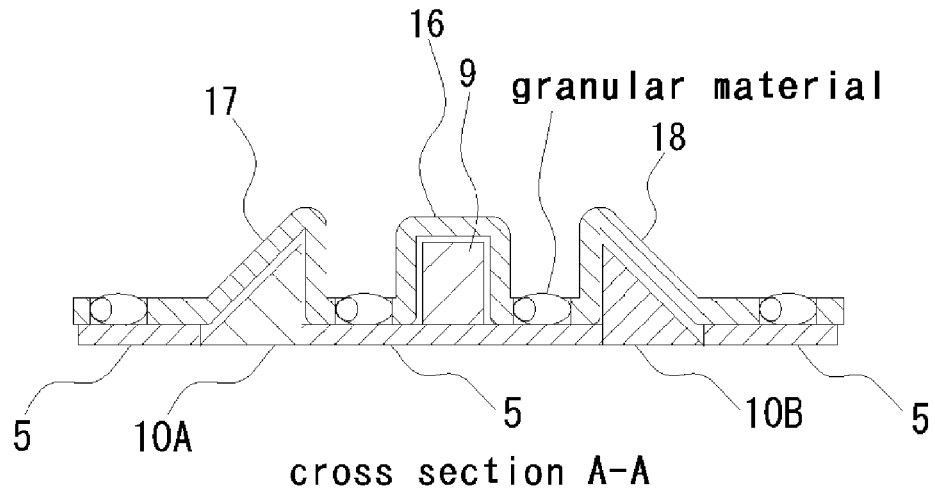
FIG. 9 is a cross-sectional view taken at A-A of FIG. 8.

FIG. 9 is a view taken at cross section A-A of FIG. 8, showing the state where the granular materials are fit in the holes 20 and 20A.

In the state where the granular materials are placed in the holes 20 and 20A, the alignment device 2 (the tray 3 and the alignment plate 4) is placed in a still manner on the reading surface of the image reading device 1. Then, the handles 19 of the alignment plate 4 are held, and the alignment plate 4 is removed upward from the tray 3 as shown in FIG. 1. At this time, the granular materials fit in the holes 20 and 20A all remain placed on the bottom plate 5 of the tray 3. Since the shapes of the holes 20 and 20A are designed to control the direction of the granular materials, the granular materials are placed in orderly aligned manner with the long axes arranged in the same direction.

The shapes of the granular materials placed on the bottom plate 5 of the tray 3 are taken in as image via the image reading device 1. At this time, since both the planar view image and the side view image of the granular materials placed between the reflective element 10A and the background 9 and between the reflective element 10B and the background 9 are taken, not only the length and width but also the thickness of the granular materials can be measured.

Now, the mechanism for taking the side view image of the granular materials will be described.

Figure 10:
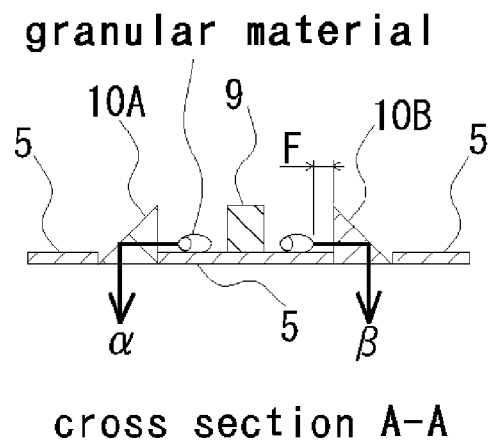
FIG. 10 is a cross-sectional view of the tray showing a state in which granular materials are placed thereon according to example 1 of the present invention.

FIG. 10 is a cross-sectional view (cross section taken at A-A of FIG. 3) of the tray 3 showing the state in which the granular materials are placed between the reflective elements 10A and 10B and the background 9. Normally, when an image is taken using a scanner for measuring dimension, only the surface of the granular materials facing the reading surface of the scanner is taken in the image. In contrast according to the present example, prisms are disposed as reflective elements 10A and 10B, so that light including image information of the surface of the granular materials in the thickness direction placed on the bottom plate 5 of the tray 3 is bent and guided via the prisms in the direction of arrows a and p, that is, the direction toward the reading surface of the image reading device 1. Therefore, the image of the granular materials in the thickness direction can also be taken via the image reading device 1.

Further, when using prisms as the reflective elements 10A and 10B, the prisms should have cross sections shaped as isosceles right triangles as shown in FIG. 10, wherein one side of the isosceles is faced toward the side surface of the granular materials and the other side is arranged to face the reading surface of the image reading device 1.

Figure 11:
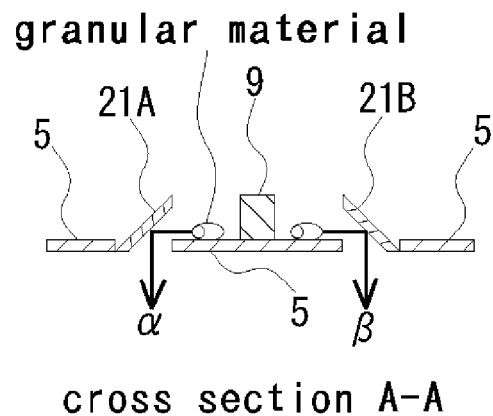
FIG. 11 is a cross-sectional view of the tray in which mirrors are used as reflective elements according to example 1 of the present invention.
Figure 12:
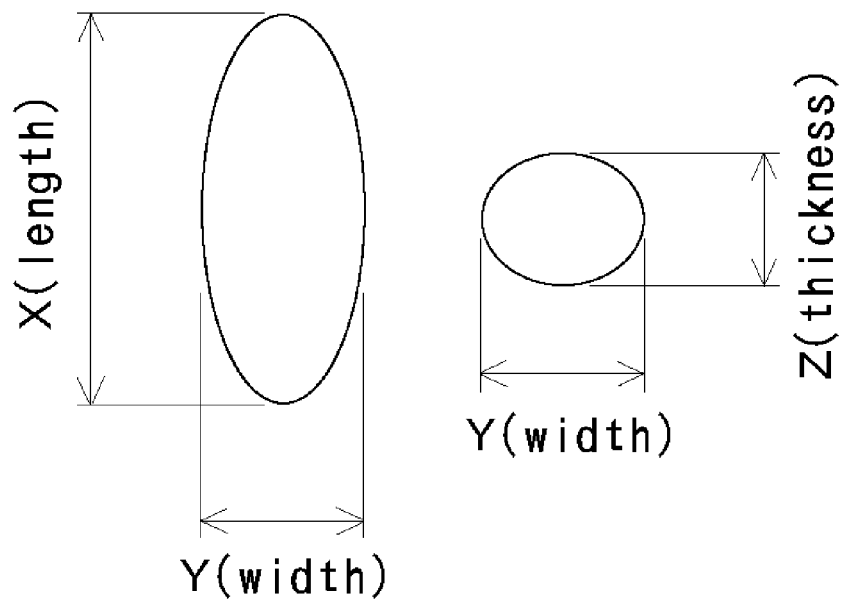
FIG. 12 is a view showing the three-axis directions of the granular material.

Mirrors can be used instead of the prisms as the reflective elements 10A and 10B. FIG. 11 is a cross-sectional view of the tray 3 in which mirrors are used as the reflective elements 10A and 10B. By arranging a mirror 21A as the reflective element 10A and a mirror 21B as the reflective element 10B, the light including image information of the surface in the thickness direction of the granular materials placed on the bottom plate 5 of the tray 3 is bent and guided via the mirrors 21A and 21B in the direction of arrows a and p, that is, the direction of the reading surface of the image reading device 1. Therefore, the image of the granular materials in the thickness direction can also be taken via the image reading device 1.

The reflecting surface of the mirrors 21A and 21B can be a flat surface, or can also be a convex or a concave surface according to the object of measurement.

An example in which a single background is arranged has been described according to the present example, but the number of backgrounds is not restricted to one, and a plurality of backgrounds can be disposed if there is enough room on the bottom plate 5 of the tray 3. At this time, by arranging the reflective elements to correspond to the number of backgrounds disposed, it becomes possible to increase the number of granular materials capable of having their thicknesses measured.

Now, reference character F shown in FIG. 10 will be described. Reference character F denotes the distance between the granular materials and the reflective elements 10A and 10B. The measurement result will be affected if the distance F is not fixed, but according to the present example, the granular materials are aligned and positioned using the alignment plate 4, so that the distance F between the granular materials and the reflective elements 10A and 10B is fixed. When the granular materials are rice grains, the distance F should be set between 0.5 mm and 1.5 mm, preferably between 0.8 mm and 1.2 mm, and more preferably approximately 1.0 mm.

Example 2

FIGS. 13 through 20 show explanatory views of example 2 of the present invention.

Figure 13:
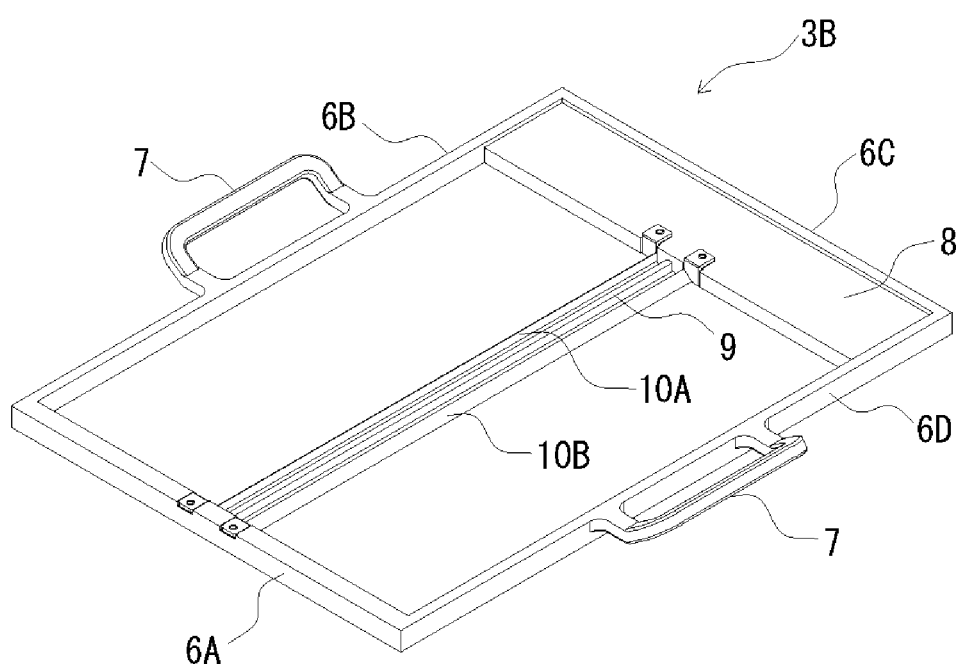
FIG. 13 is a perspective view of an alignment frame body according to example 2 of the present invention.

The alignment device 2 is composed of a tray 3 and an alignment plate 4 according to example 1, but an alignment device 2B can also be composed of an alignment frame body 3B and an alignment plate 4. FIG. 13 shows an alignment frame body 3B according to example 2. The greatest difference between the alignment frame body 3B and the tray 3 is the presence and absence of a bottom plate 5. In other words, the alignment frame body 3B is formed by removing the bottom plate 5 from the tray 3. Therefore, the components which are common to the tray 3 are denoted with the same reference numbers in the description.

Figure 15:
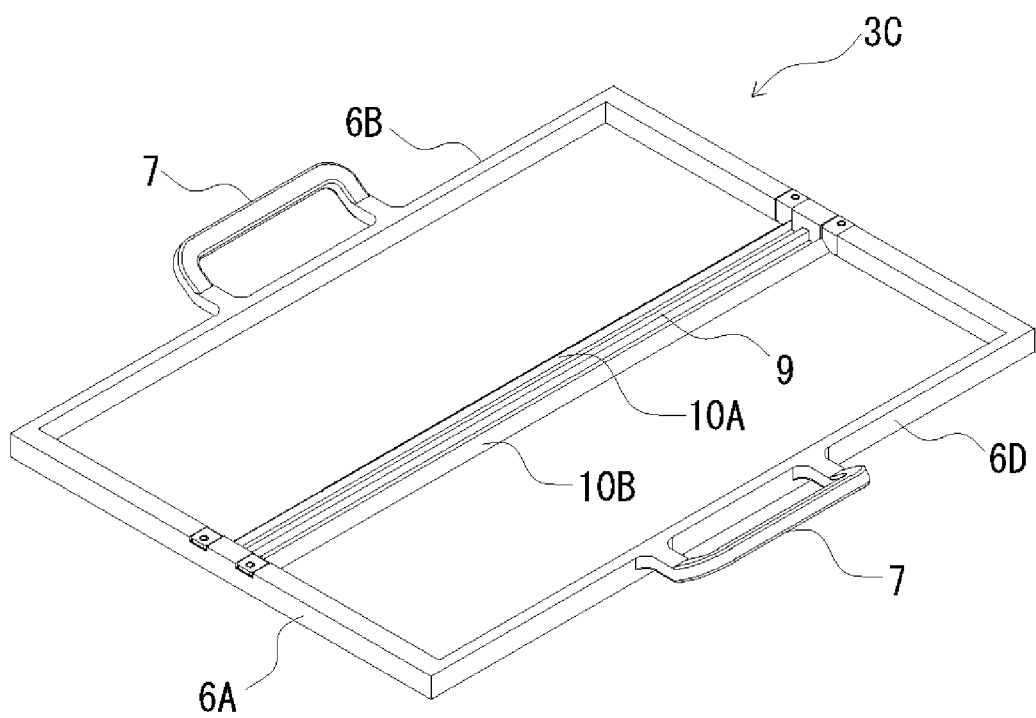
FIG. 15 is a perspective view of the alignment frame body according to example 2 of the present invention.

Similar to example 1, if only the three axes of the granular materials are to be measured, there is no need to dispose the reference plate, as shown in the alignment frame body 3C of FIG. 15. Since the alignment frame body 3C does not have a reference plate, the background 9 is disposed in a suspended manner between the two opposing side walls 6A and 6C. In this case, both ends of the background 9 should be fixed for example by bonding the surfaces of the ends coming in contact with the side walls 6A and 6C. The background 9 can also be arranged in a suspended manner on the side walls 6B and 6D.

As for the alignment frame body 3C, an alignment plate is used in a similar manner as the tray 3 and the alignment frame body 3B. As for the alignment plate used in this example, the size of the alignment plate 4 should be varied to correspond to the alignment frame body 3C.

Figure 14:
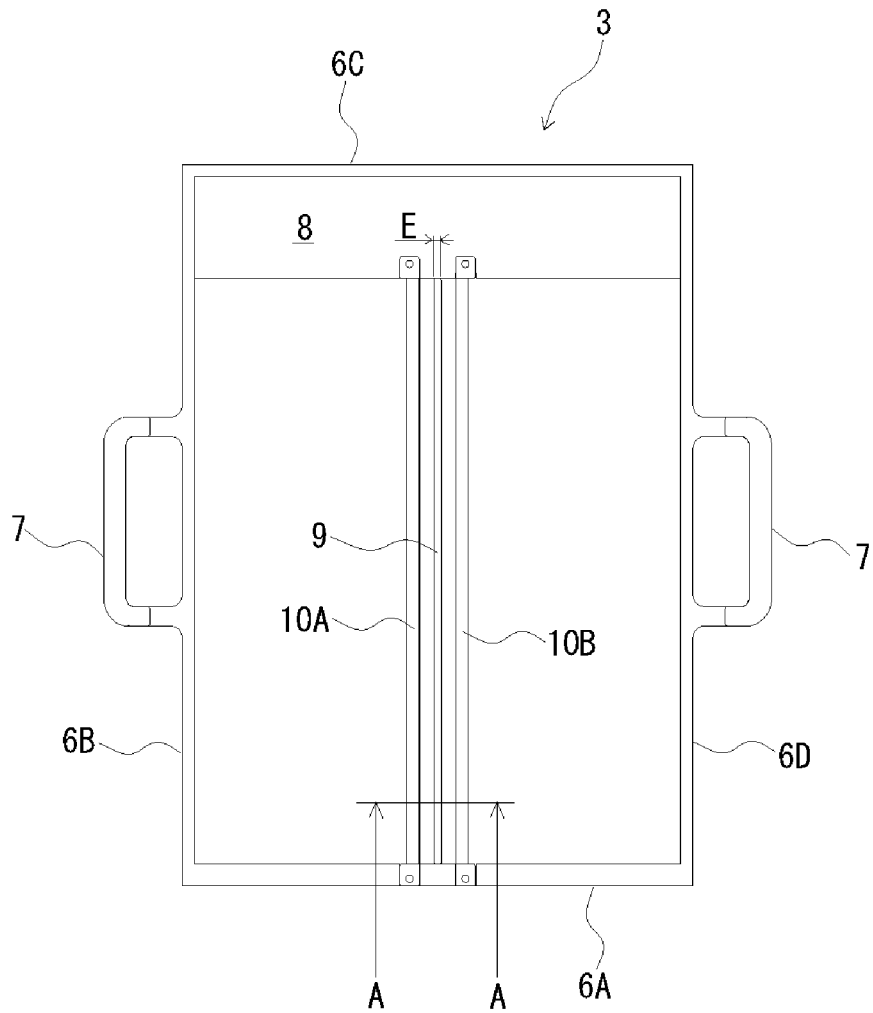
FIG. 14 is a plan view and a partial cross-sectional view of the alignment frame body according to example 2 of the present invention.
Figure 14:
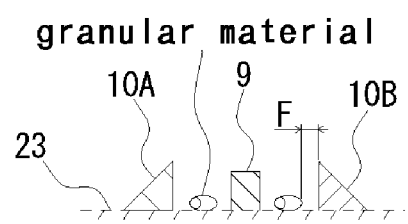

As shown in the partial cross-sectional view (cross section A-A) of FIG. 14, since the alignment frame body 3B does not have a bottom plate, the bottom side of the background 9 and the reflective elements 10A and 10B should be arranged to contact the reading surface 23 when the frame body 3B is placed on the reading surface 23 of the image reading device 1.

Next, the method for using an alignment device 2B according to the present example will be described.

First, the alignment frame body 3B is placed still on the reading surface 23 of the image reading device 1. In that state, the alignment plate 4 is fit from above to the alignment frame body 3B. At this time, the lower side of the alignment plate 4 is in contact with the reading surface 23. Next, a plurality of granular materials are poured onto the upper surface of the alignment plate 4. At this time, granular materials are poured into areas between the protruded section 16 for the background and the protruded section 17 for the reflective element and between the protruded section 16 for the background and the protruded section 18 for the reflective element so that the granular materials are also fit in the holes 20A formed in those areas. Then, the surface of the granular materials is evened out manually so that the granular materials are fit in the holes 20 and 20A of the alignment plate 4.

Figure 16:
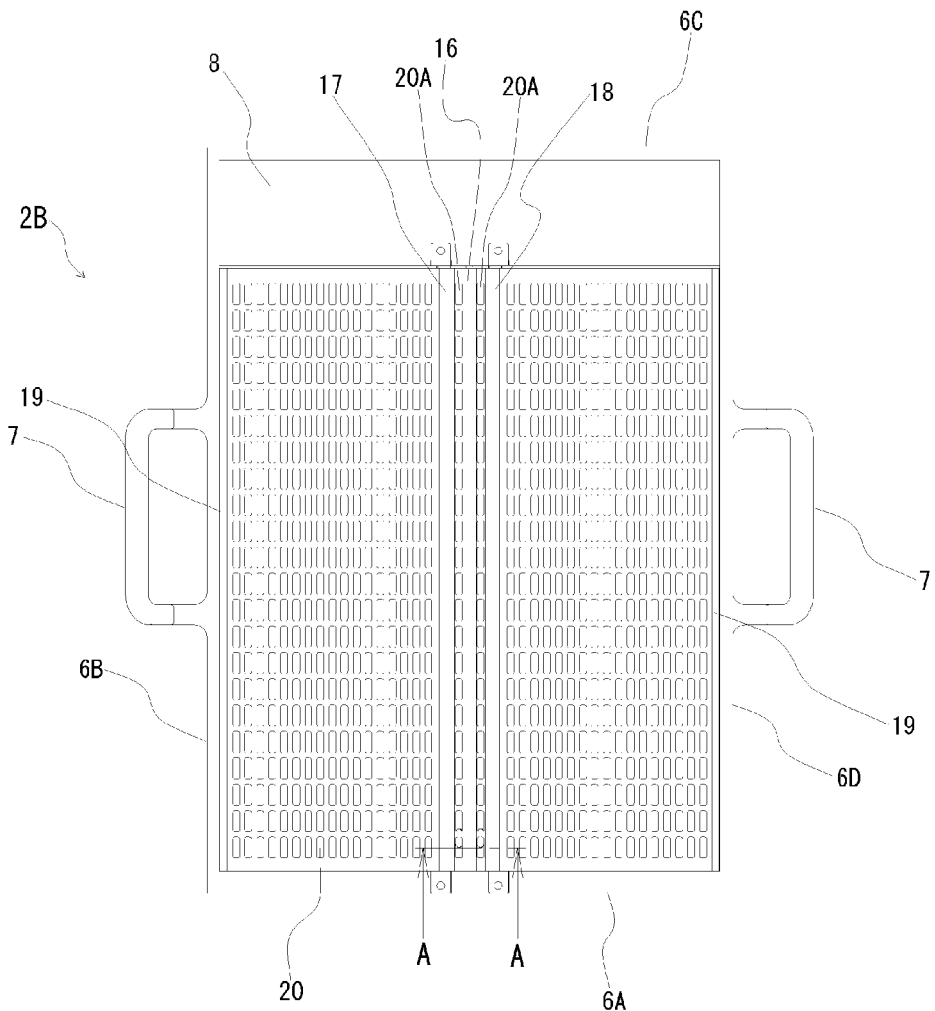
FIG. 16 is a plan view of the alignment frame body according to example 2 of the present invention.
Figure 17:
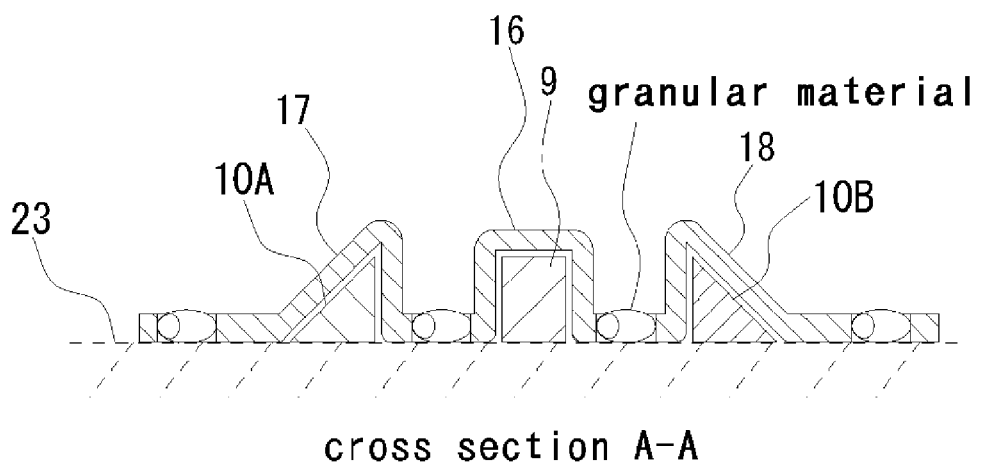
FIG. 17 is a cross-sectional view taken at A-A of FIG. 16.

FIG. 16 is a plan view of the alignment device 2B showing the state in which the alignment plate 4 is fit to the alignment frame body 3B. Further, FIG. 17 is a view showing the cross section taken at A-A of FIG. 16, showing the state in which the granular materials are fit in the holes 20 and 20A.

Figure 18:
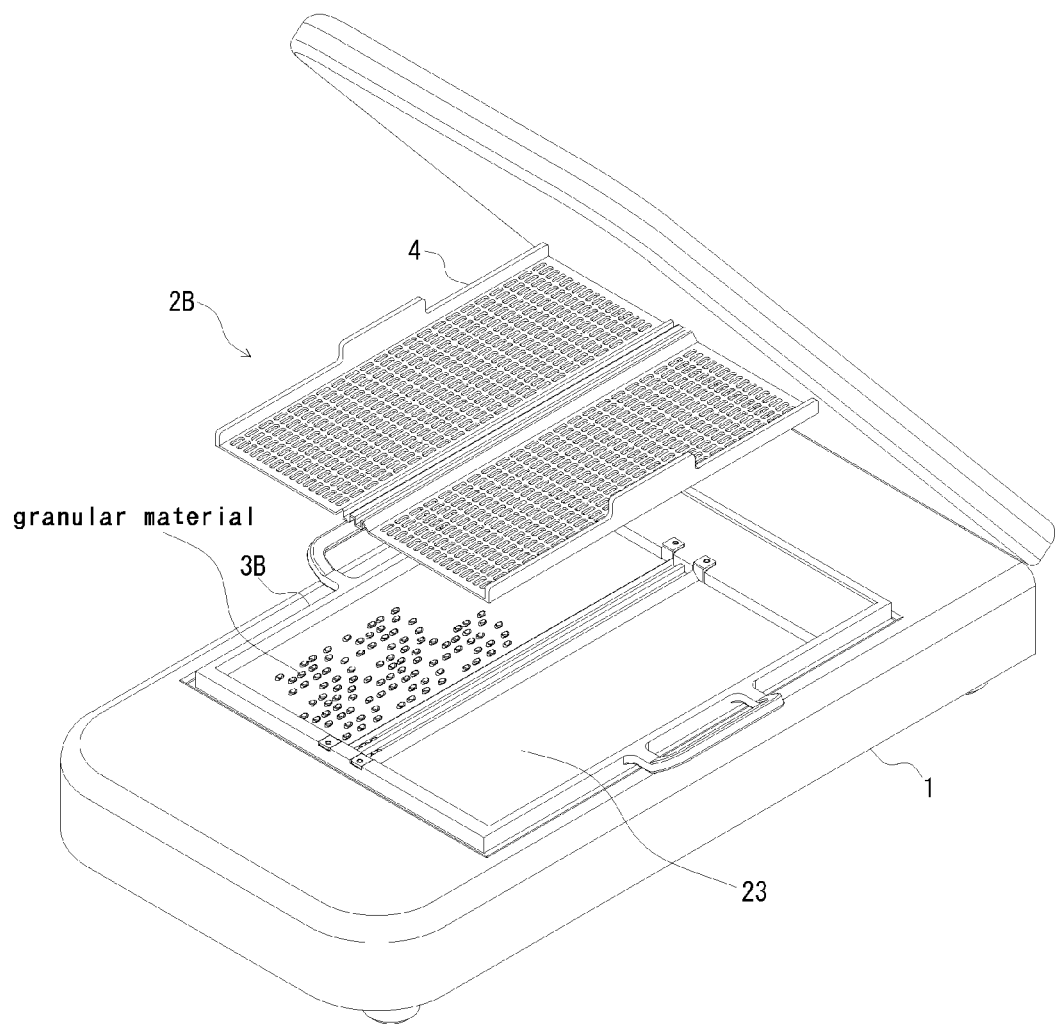
FIG. 18 is a perspective view showing a state in which the alignment frame body is set to the image reading device according to example 2 of the present invention.

In the state where the granular materials are fit in the holes 20 and 20A, as shown in FIG. 18, the handles 19 of the alignment plate 4 are held, and the alignment frame body 3B is removed upward. At this time, the granular materials fit in the holes 20 and 20A all remain placed on the reading surface 23 of the image reading device 1. Since the shapes of the holes 20 and 20A are designed to control the direction of the granular materials, the granular materials are placed in orderly aligned manner with the long axes arranged in the same direction.

The shapes of the granular materials placed on the reading surface 23 are taken in as image via the image reading device 1. At this time, since both the planar view image and the side view image of the granular materials placed between the reflective element 10A and the background 9 and between the reflective element 10B and the background 9 are taken, not only the length and width but also the thickness of the granular materials can be measured.

Now, the mechanism for taking the side view image of the granular materials will be described.

Figure 19:
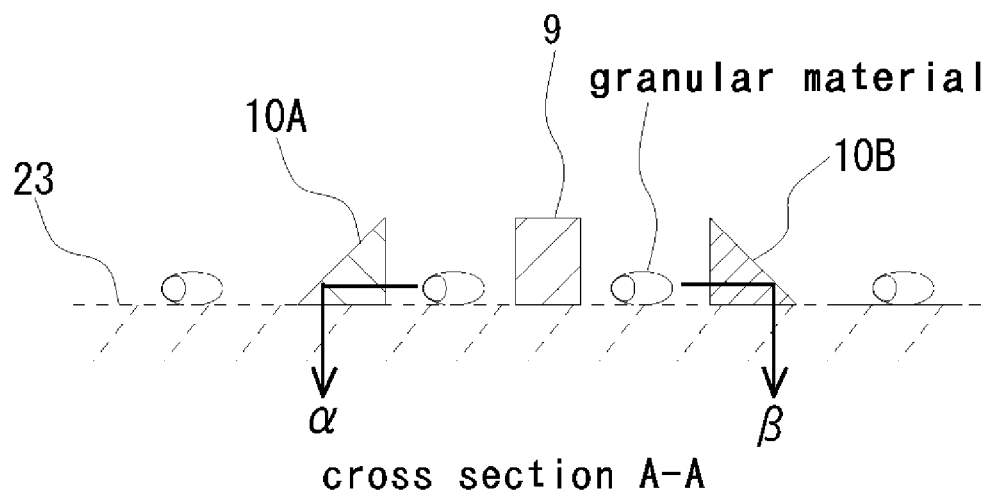
FIG. 19 is a cross-sectional view of the alignment frame body showing a state in which the granular materials are place thereon according to example 2 of the present invention.

FIG. 19 is a cross-sectional view (cross section taken at A-A of FIG. 14) of the alignment frame body 3B showing the state in which the granular materials are placed between the reflective element 10A and the background 9 and between the reflective element 10B and the background 9 after the alignment plate 4 has been removed. Normally, when an image is taken using a scanner, only the surface of the granular materials facing the reading surface 23 of the scanner is taken in as image. In contrast according to the present example, prisms are disposed as reflective elements 10A and 10B, so that light including image information of the surface of the granular materials in the thickness direction placed on the reading surface 23 is bent and guided in the direction of arrows a and p, that is, the direction toward the reading surface of the image reading device 1. Therefore, the image of the granular materials in the thickness direction can also be taken via the image reading device 1.

Further, when using prisms as the reflective elements 10A and 10B, the prisms should have cross sections shaped as isosceles right triangles as shown in FIG. 19, wherein one side of the isosceles is faced toward the side surface of the granular materials and the other side is arranged to face the reading surface of the image reading device 1.

Figure 20:
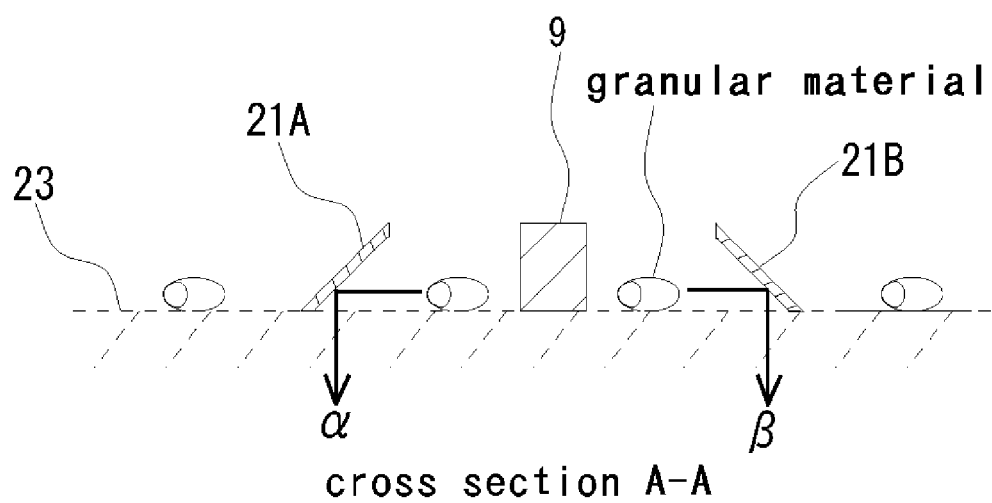
FIG. 20 is a cross-sectional view of the alignment frame body in which mirrors are used as reflective elements according to example 2 of the present invention.

According to the present example, mirrors can be used instead of the prisms as the reflective elements 10A and 10B. FIG. 20 is a cross-sectional view of the alignment frame body 3B in which mirrors are used as the reflective elements 10A and 10B. By arranging a mirror 21A as the reflective element 10A and a mirror 21B as the reflective element 10B, the light including image information of the surface in the thickness direction of the granular materials placed on the reading surface 23 is bent and guided via the mirrors 21A and 21B in the direction of arrows a and p, that is, the direction of the reading surface of the image reading device 1. Therefore, the image of the granular materials in the thickness direction can also be taken via the image reading device 1.

The reflecting surface of the mirrors 21A and 21B can be a flat surface, but the surface can also be a convex or a concave surface according to the object of measurement.

The alignment frame body 3C can also use prisms and mirrors as the reflective elements 10A and 10B, similar to the alignment frame body 3B.

An example in which a single background is arranged has been described according to the present example, but the number of backgrounds is not restricted to one, and a plurality of backgrounds can be disposed. At this time, by arranging the reflective elements to correspond to the number of backgrounds disposed, it becomes possible to increase the number of granular materials capable of having their thicknesses measured.

The present example enables granular materials to be arranged and placed in an orderly aligned manner, which can be suitably applied not only to grains such as rice grains and wheat grains but also to other materials having granular shapes, such as resin pellets.

REFERENCE SIGNS LIST 1 image reading device
2 alignment device
2B alignment device
3 tray
3B alignment frame body
3C alignment frame body
4 alignment plate
5 bottom plate
6A side wall
6B side wall
6C side wall
6D side wall
7 handle
8 reference plate
9 background (background panel)
10A reflective element
10B reflective element
11 slit
12 mounting section
13 groove
14 hole
15 projection
16 protruded section for background
17 protruded section for reflective element
18 protruded section for reflective element
19 handle
20 holes
20A holes
23 reading surface of image reading device 1

The invention claimed is:

1. A tray for placing granular materials on a reading surface of an image reading device such as a scanner, comprising:
a transparent bottom plate;
one or a plurality of nontransparent backgrounds vertically upstanding relative to the bottom plate to a height higher than a thickness of the granular materials; and
one or a plurality of reflective elements arranged at predetermined intervals in parallel with the background;
wherein an alignment plate is fit from an upper direction to the bottom plate of the tray, the alignment plate comprising a protruded section for the background for covering the background, a protruded section for the reflective element disposed in parallel with the protruded section for the background for covering the reflective element, and a plurality of holes having a shape similar to the shape of the granular materials, the granular materials being poured into the holes of the alignment plate fit to the bottom plate so that the granular materials are placed in orderly aligned manner on the bottom plate including the area between the background and the reflective element, and
regarding the granular materials placed between the background and the reflective element of the granular materials placed on the bottom plate, a light from a thickness direction of the granular materials is bent and guided via the reflective element to an optical axis direction of an imaging means of the image reading device, so that not only planar images in a longitudinal direction and a width direction of the granular materials but also a side view image in the thickness direction of the granular materials can be received via the imaging means.

2. The tray according to claim 1, wherein the reflective element is composed of a prism or a mirror.

3. The tray according to claim 1, wherein the granular materials placed between the background and the reflective element are placed at a predetermined distance away from the reflective element via the alignment plate.

4. An alignment frame body, wherein a bottom plate is removed from a frame body of the tray according to claim 1 in which the tray is formed by attaching the bottom plate to a lower side of the frame body, so that granular materials are placed directly on the reading surface of the image reading device to take in image.

5. The tray according to claim 2, wherein the granular materials placed between the background and the reflective element are placed at a predetermined distance away from the reflective element via the alignment plate.

6. An alignment frame body, wherein a bottom plate is removed from a frame body of the tray according to claim 2 in which the tray is formed by attaching the bottom plate to a lower side of the frame body, so that granular materials are placed directly on the reading surface of the image reading device to take in image.

7. An alignment frame body, wherein a bottom plate is removed from a frame body of the tray according to claim 3 in which the tray is formed by attaching the bottom plate to a lower side of the frame body, so that granular materials are placed directly on the reading surface of the image reading device to take in image.

8. An alignment frame body, wherein a bottom plate is removed from a frame body of the tray according to claim 5 in which the tray is formed by attaching the bottom plate to a lower side of the frame body, so that granular materials are placed directly on the reading surface of the image reading device to take in image.

* * * * *